United States Patent
Indiano

(10) Patent No.: US 9,028,530 B2
(45) Date of Patent: May 12, 2015

(54) SUTURE HAVING ANTIMICROBIAL PROPERTIES

(75) Inventor: Ignazio Mi Indiano, Yardley, PA (US)

(73) Assignee: IM Indiano, LLC, Indianapolis, IN (US)

(*) Notice: Subject to any disclaimer, the term of this patent is extended or adjusted under 35 U.S.C. 154(b) by 138 days.

(21) Appl. No.: 13/136,963

(22) Filed: Aug. 16, 2011

(65) Prior Publication Data

US 2012/0041483 A1 Feb. 16, 2012

Related U.S. Application Data

(60) Provisional application No. 61/374,040, filed on Aug. 16, 2010.

(51) Int. Cl.
*A61B 17/04* (2006.01)
*A61B 17/06* (2006.01)
*D07B 1/02* (2006.01)
*A61B 17/00* (2006.01)

(52) U.S. Cl.
CPC . *A61B 17/06166* (2013.01); *A61B 2017/00526* (2013.01); *A61B 2017/00889* (2013.01); *A61B 2017/06019* (2013.01); *D07B 1/02* (2013.01); *D07B 2401/205* (2013.01)

(58) Field of Classification Search
USPC .................................. 606/228; 428/364–378
See application file for complete search history.

(56) References Cited

U.S. PATENT DOCUMENTS

| 861,231 | A | | 7/1907 | Clark |
| 4,024,871 | A | * | 5/1977 | Stephenson ................... 606/231 |
| 4,470,941 | A | * | 9/1984 | Kurtz ............................. 264/136 |
| 4,641,504 | A | | 2/1987 | Runkel et al. |
| 5,380,580 | A | * | 1/1995 | Rogers et al. ................. 428/219 |
| 6,878,757 | B2 | | 4/2005 | Robey |
| 7,513,093 | B2 | | 4/2009 | Scalzo et al. |
| 7,882,688 | B2 | | 2/2011 | Indiano |
| 7,886,515 | B2 | | 2/2011 | Indiano |
| 2004/0074589 | A1 | * | 4/2004 | Gessler et al. ................ 156/155 |
| 2007/0010856 | A1 | | 1/2007 | Cohen |
| 2009/0131979 | A1 | * | 5/2009 | Thompson et al. ........... 606/224 |
| 2010/0000196 | A1 | | 1/2010 | Indiano |
| 2010/0113871 | A1 | * | 5/2010 | Dias et al. ..................... 600/101 |
| 2010/0166832 | A1 | * | 7/2010 | Ingle et al. .................... 424/443 |

OTHER PUBLICATIONS

Ford HR, Jones P., Reblock K, Simpkins DL, "Intra-operative Handling and Wound Healing Characteristics of Coated Polyglatin 910 Antibacterial Suture and Coated Polyglactin 910 Suture", *Surg. Infec. 2005*; 6; 313-21.

(Continued)

*Primary Examiner* — Gregory Anderson
*Assistant Examiner* — Christina Lauer
(74) *Attorney, Agent, or Firm* — E. Victor Indiano; Indiano Law Group, LLC

(57) ABSTRACT

A tissue engageable suture having antimicrobial properties is provided. The suture includes a plurality of thread members. The thread members include a plurality of structural thread members having a structural portion and an antimicrobial portion. The thread members also include a plurality of adhesive thread members. The plurality of structural thread members and the plurality of adhesive thread members are woven together to form a multiple thread-containing cabled suture wherein the adhesive thread members bond the structural thread members within the cabled structure.

18 Claims, 2 Drawing Sheets

(56) References Cited

OTHER PUBLICATIONS

Storch ML, Rothenberger SJ, Jacinto G, "Experimental Efficacy Study of Coated VICRYL + Antibacterial Suture in Guinea Pigs Challeneged with *Staphylococcus aures*", *Surg. Infect. J. 2004*; 5; 2A1-288.

Polymecix Press Release dated Jun. 11, 2010 "New Grant Supports Development of Antimicrobial Sutures to Combat Infection", www.newswise.com/articles.

\* cited by examiner

SUTURE HAVING ANTIMICROBIAL PROPERTIES

I. PRIORITY STATEMENT

The instant application claims benefit of priority to Ignazio M. Indiano, U.S. Provisional Patent Application for SUTURE HAVING ANTIMICROBIAL PROPERTIES filed on 16 Aug. 2010 as Ser. No. 61/374,040, which application is fully incorporated herein by reference.

II. TECHNICAL FIELD OF THE INVENTION

The present invention relates to sutures used in medical applications, and more particularly to a suture having antimicrobial properties.

III. BACKGROUND OF THE INVENTION

Sutures are employed to engage tissue to do things such as closing wounds and/or surgical site incisions, or to repair tissue that has torn. When using a suture, it is important to avoid infection. Although surgeries and wound closings are often performed under sterile conditions, surgical-site infections (SSIs) are the third most commonly acquired hospital infection, and may be associated with severe morbidity and mortality. Since more than sixty percent (60%) of SSIs occur in the area of the incision, the use of sutures having antimicrobial properties has the potential to be useful in combating such infections, and ultimately, hopefully improving patient outcomes by reducing the amount and severity of these SSI type infections.

Sutures having antimicrobial properties exist currently. At the present time, the industry leader in the antimicrobial suture market is believed to be Ethicon, a Johnson & Johnson Company. Johnson & Johnson's Ethicon antibacterial sutures rely primarily on a triclosan-type antibiotic agent.

Triclosan is a chlorinated phenolic biocide antiseptic that, according to Johnson & Johnson has a different mode of action than antibiotics. It is a "phenol" with multi-targeted biocidal mechanisms, that is believed to have non-specific effects that act on cell membrane activities to kill undesired microbes. It is also believed that Triclosan blocks the active site of the Enoyl-acyl Carrier Protein Reductase (ENR) that is an essential enzyme in fatty acid synthesis, used in building cellular components and reproduction.

The Ethicon triclosan coated sutures appear to be able to perform their function in a workmanlike manner. To date, published data exists to suggest that Triclosan inhibits bacteria colonization of a suture. See, Ford H R, Jones P., Reblock K, Simpkins D L, "Intra-operative Handling and Wound Healing Characteristics of Coated Polyglatin 910 Antibacterial Suture and Coated Polyglactin 910 Suture" Surg. Infec. 2005; 6; 313-21.

Additionally, an in vivo study of the Triclosan sutures showed that they have a bactericidal activity against staph and inhibitory or bactericidal activity against S Aureus, Methicillin-Resistant S Aureus, MRSA; S Epidermidis (Biofilm-Positive) and E-coli. See, Storch M L, Rothenberger S J, Jacinto G, "Experimental Efficacy Study of Coated VICRYL+Antibacterial Suture in Guinea Pigs Challenged with Staphylococcus Aures". Surg. Infect. J. 2004; 5; 2A1-288.

Additional information about the Ethicon sutures can be found on Ethicon's web site at http://www.plussutures.com. Additional discussions of Ethicon's antimicrobial sutures can be found in Stephenson, U.S. Pat. No. 4,024,871 (24 May 1997) and Scalzo et al., U.S. Pat. No. 7,513,093 (7 Apr. 2009). In particular, the reader's attention is directed to the prior art discussions in each of these Ethicon patents, as a wide variety of various antimicrobial agents and methods for incorporating antimicrobial agents into sutures are discussed therein. These disclosures are incorporated herein by reference.

In addition to Ethicon, the Tyco Healthcare Group has also been quite active in the antimicrobial suture field. An example of a Tyco suture is discussed in Robey, U.S. Pat. No. 6,878, 757 (12 Apr. 2005), that discloses an antimicrobial suture coating that contains a fatty acid Ester salt mixed with a bioabsorbable co-polymer.

Another Tyco patent application is Cohen, U.S. Published Application No. US2007/0010856 A1, having a publication date of 11 Jan. 2007. Cohen's suture includes a plurality of filaments with interstitial spaces defined by the plurality of filaments, and an antimicrobial solution within the interstitial spaces. An antimicrobial coating is placed on at least a portion of the plurality of filaments. The suture is attached to a needle to produce a needle containing suture. The preferred antimicrobial agent used in Cohen is an antiseptic, film-forming polymer, and a salt of a fatty acid ester. Examples of same are given in paragraph [0014] of the Cohen published patent application.

Additionally, a company named Polymedix has developed an antimicrobial suture, for which they recently received a funding grant. The Polymedix suture employs Poly Cide polymers, that are described as "novel defensinminetic compounds," that are described as synthetic mimetics of the host offense proteins, that, (according to Polymedix) are one of the oldest and most effective antimicrobial defense systems found in humans and virtually all living creatures. These Poly Cides are alleged to have a mechanism of action that directly disrupts the bacterial cell membranes, that makes the development of bacterial resistence unlikely to occur. More information about these sutures can be found on www.polymedix.com. See Polymecix Press Release dated 11 Jun. 2010 "New Grant Supports Development of Antimicrobial Sutures to Combat Infection". See http://www.newswise.com/articles. No admission or position is taken as to whether the Polemedix compounds constitute prior art to the instant invention.

Silver is another compound having well known antimicrobial properties that has been used to incorporate antimicrobial properties into particular articles. One old example of silver being used in a ligature is shown in A. W. Clark, U.S. Pat. No. 861,231 dated 23 Jul. 1907. Clark created a surgical ligature that was soaked in an antiseptic salt that preferably comprised a iodide of silver as the insoluble salt.

Another example of a use silver in a textile product (non-suture related), to create an antimicrobial textile product containing silver is shown in Ignazio M. Indiano, U.S. Published Patent Application No. 2010/0000196.

Although the above referenced devices no doubt perform their intended function in a workmanlike manner, room for improvement exists. In particular, room for improvement exists in providing an antimicrobial suture, that is both capable of having significant antimicrobial properties, and that can be produced at a reasonable cost, to provide a cost-effective deterrent for the growth of infections.

III. SUMMARY OF THE INVENTION

In accordance with the present invention, a tissue engageable suture having antimicrobial properties is provided. The suture comprises a plurality of thread members. The thread members include a plurality of structural thread members having a structural portion and an antimicrobial portion. The thread members also include a plurality of adhesive thread members. The plurality of structural thread members and the plurality of adhesive thread members are woven together to form a multiple thread-containing cabled suture wherein the adhesive thread members bond the structural thread members within the cabled structure, Preferably, the structural thread includes a structural portion containing a monofilament core, having an exterior surface and an antimicrobial portion. Preferably, the antimicrobial portion comprises a metal having antimicrobial properties that is applied to the exterior surface of the monofilament core. The monofilament core preferably comprises a monofilament formed from a material selected from a group consisting of plastic and cellulose. The metal having antimicrobial properties preferably comprises silver. Preferably, the silver is purified so that it achieves a purity level of at least about 98% pure silver, and most preferably, of at least about 99% pure silver.

In a preferred embodiment, the adhesive thread is comprised of a separation yarn that serves as the adhesive. An example of such a separation yarn is a GRILON® separation yarn. GRILON® is a registered trademark of EMS-CHEMIE AG Corporation of DOMAT/EMS Switzerland. One or more GRILON® threads are joined with a plurality of silver plated monofilament threads to form the cable-like suture.

In a most preferred embodiment, the GRILON® is a relatively low melting GRILON®, that melts at a temperature below body temperature.

In accordance with another aspect of the present invention, a method is provided for manufacturing a tissue engageable suture having antimicrobial properties. The method comprises providing a plurality of monofilament thread members and a purified silver having a purity of at least about 90%. An exterior surface of the monofilament thread members is coated with the purified silver to form structural thread members having a structural portion and an antimicrobial portion. A plurality of adhesive thread members are also provided. The structural thread members are woven together with the adhesive thread members to form a cabled suture containing adhesive thread members interspersed among the structural thread members, wherein the adhesive thread members bond the structural thread members for preventing the cabled sutures from unraveling. The cabled suture is then heated to volatilize off over about 90% of the adhesive material of the adhesive thread members.

One feature of the present invention is that it includes structural threads that include a monofilament core, that is plated with an antimicrobial metal, such as silver. This feature has the advantage of enabling the suture manufacturer to create a suture that has good "suture" properties including sufficient tensile strength to avoid breakage and sufficient bendablity and malleability to be able to act like highly bendable thread, while still possessing antimicrobial activities provided by the metal.

Another feature of the present invention is that a separation yarn is employed. The separation yarn is employed as an adhesive to bind the structural threads together. This feature has the advantage of preventing structural threads that are woven together in a cable-like suture, from becoming unraveled.

Another feature of the present invention is that the separation yarn employed is a separation yarn that will melt and partially evaporate at certain temperatures. This feature has the advantage of reducing the potential for the separation yarn to form a coating on the silver or other antimicrobial property-containing metal, that inhibits the antimicrobial effect of the antimicrobial property-containing metal.

Another feature of the present invention is that the weight percent of silver in the structural threads of the present invention is preferably less than 20% of the weight percent of the monofilament for external use threads, and preferably less than about 25% for internally used sutures. This feature has the advantage of helping to reduce the amount of silver employed in the thread, while still achieving significant antimicrobial properties. By reducing the amount of silver employed, the threads can be made more cost-effective.

These and other features will become apparent to those skilled in the art upon a review of the drawings and detailed description presented below, that present the best mode of practicing the present invention perceived at the current time by the Applicant.

III. BRIEF DESCRIPTION OF DRAWINGS

FIG. 1 is a schematic plan view of a suture system of the present invention that includes a multi-thread (multi-filament) cabled suture 14, having a first end attached to a surgical needle 12, here shown as a surgical needle 12 having a 90° bend;

IV. DETAILED DESCRIPTION OF THE INVENTION

Prior art antimicrobial sutures exist. Antimicrobial properties are beneficial to incorporate into sutures to combat the growth of microbes and germs, and the creation and spread of infections by these microbes and germs. Such infections are complicating and deleterious events that often accompany the use of sutures used to close a wound or surgical site. By killing microbes and/or retarding the growth of microbes, one reduces the chance and/or severity of infection, thus helping to speed the healing process and increasing the success rates of procedures.

As silver is a known antimicrobial agent, it would seem logical to employ a silver strand as a suture, to take advantage of the antimicrobial properties of silver. Unfortunately, such a strand will not work well as a suture because a strand of silver likely does not have sufficient tensile strength to hold the tissue together without breaking, when the suture is used to sew up a wound. Additionally, a silver strand would likely not be sufficiently malleable to work well. Malleability relates to the ability of the silver fiber to be bendable and flexible. In summary, a silver strand would likely not be strong enough would be too brittle to serve well as a suture.

Figure 1:
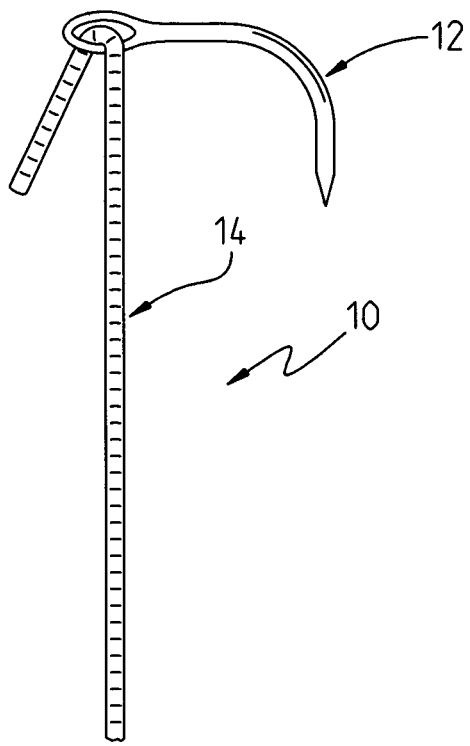

In order to overcome these draw backs with the use of pure silver strands, the present invention employs a novel silver plated plastic monofilament structural thread as a component of a multi-filament suture. Turning now to FIG. 1, a suture system 10 of the present invention is shown. The suture system 10 comprises the final assembled product and preferably comprises a multi-filament cabled suture 14, that is coupled to a surgical needle 12.

Figure 2:
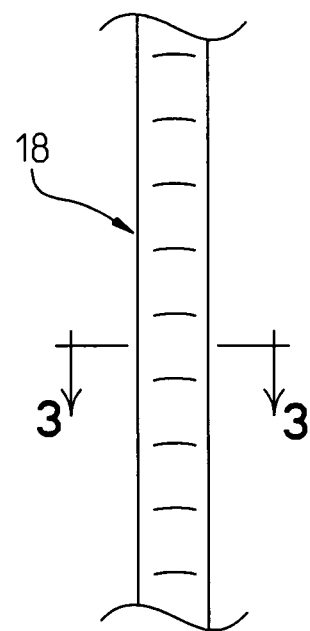
FIG. 2 is a side, schematic view of a representative thread segment.
Figure 3:
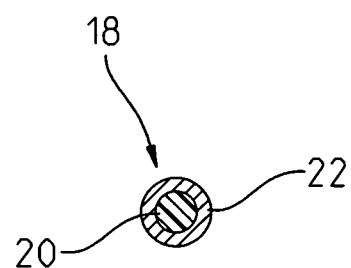
FIG. 3 is a sectional view taken along lines 3-3 of the representative thread segment of FIG. 2.

The cabled suture 14 is comprised of a plurality of cabled threads. A representative thread 18 is shown in FIGS. 2 and 3, that is comprised of at least two different types of component threads. The primary threads that are employed are the structural suture threads, such as the structural thread 18 shown in FIGS. 2 and 3. The structural threads 18 include a structural portion 20 and an antimicrobial portion 22. The structural portion 20 comprises a monofilament core 20 that is made preferably from a plastic or cellulose material, that is plated with silver to include a silver outer surface or jacket 22. The silver outer surface or jacket 22 comprises the antimicrobial portion.

Figure 5:
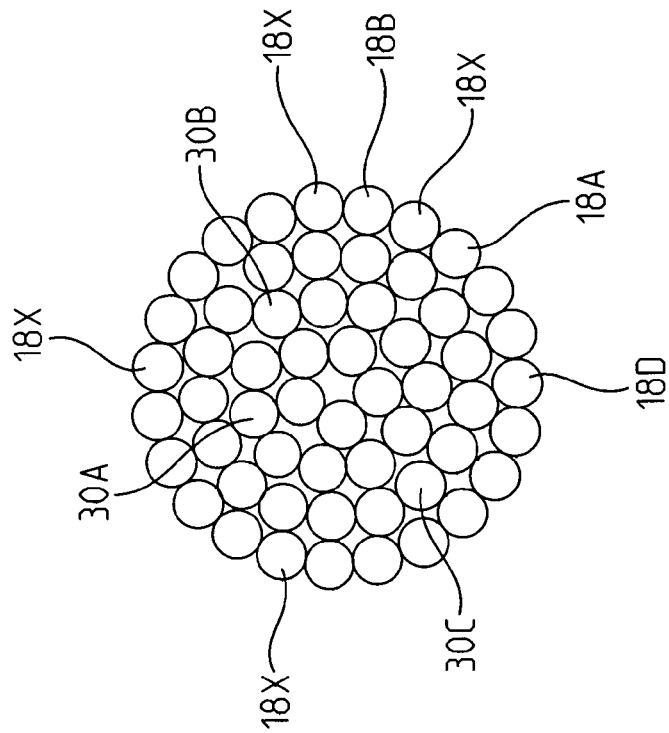
FIG. 5 is a schematic, sectional view taken along lines 5-5 of FIG. 4.

A plurality of these silver and nylon containing structural threads 18 are joined together with an adhesive, anti-separation material. An adhesive thread 300(*a-c*) made from a separation material such as GRILON® separation yarn comprises the second component thread type; and the adhesive thread 30 is joined with the silver plated monofilament structural thread 18 to form the final cabled thread 14 such as is shown in FIG. 5.

The structural threads 18 from which the suture 14 is made employ silver because of the anti-microbial properties of silver. However, strands containing only silver will not work well as a suture because silver does not have the tensile strength, nor the malleability in order to function appropriately as a tissue engaging and holding suture. To overcome these deficiencies, the Applicants' invention employs structural thread members that include a structural portion such as a nylon, mono-filament type thread.

The nylon, mono-filament type thread is similar to a plastic fishing line, except it is usually much thinner. The diameter of the nylon core is preferably at about 2.5 decitex. Decitex is a measure of the thickness or diameter of a textile fiber, and refers to the number of grams of weight of the yarn, for each ten thousand meters of the yarn. As a more general proposition, the decitex number is a number used to define the size of the yarn, or the coarseness thereof, as generally a higher decitex number relates to a coarser yarn. To some extent, "decitex" also correlates to the strength of the yarn, as a higher decitex number tends to indicate a yarn that is stronger than one with a lower decitex number. In addition to its thickness, the strength of a particular yarn is also dependant upon the type of material used for the yarn. Nonetheless, for a particular type of yarn material, a higher decitex number will usually indicate a stronger yarn. Another analogous measurement parameter is the term "denier". Denier is an American unit of measure and relates to the weight of nine thousand meters of a yarn.

The suture 14 shown in the figures as being comprised of a plurality of individual structural yarn fibers 18 (FIG. 2) wherein the structural yarn fibers have a structural portion that preferably comprises a nylon core 20. The nylon core 20 has an exterior surface that is plated with the antimicrobial portion. As such, the core is encased within an anti-microbial portion such as a silver jacket 22. In a preferred embodiment, the relative weight of the core material 20 to the silver material can be in the range of between about a 4:1 ratio, or to a 47:6 ratio. Viewed another way, in a typical structural thread, somewhere between 80% and 94% of the weight of the thread (weight percent) is comprised of the nylon core component 20, whereas somewhere between 20% and 6% of the weight (weight percent) is comprised of the silver jacket 22.

Viewed from another perspective, the use of this ratio enables the process of the instant invention to produce approximately 223,000 yards of the monofilament silver jacketed nylon structural thread 18, for every one pound of silver that is employed. The use of this ratio achieves a significant benefit by reducing the amount of silver used on a 'per unit' or per-suture basis, since the silver likely comprises the highest cost component of the final suture.

When determining the ratio between the silver and the nylon, one attempts to strike a balance. If too little silver is used, it is likely that the antimicrobial properties of the product will be adversely affected, since the silver carries the antimicrobial activity within the silver plated nylon suture yarn. On the other hand, the use of too much silver may result in the cost of the suture being driven up unnecessarily.

In another preferred embodiment, the strand 18 by weight is comprised of 92% nylon core to 8% silver plating 20 for which the suture is being placed. Presently, it is envisioned that a greater percentage of silver will be used for internal sutures, than for external sutures. For example, it is believed that internal sutures should have at least about 21% silver, and 79% or less of the nylon monofilament; and not preferably between about 21% and 25% silver by weight percent.

Another important property of the silver is that the silver employed for the plating is preferably made to be as pure as possible. In this regard, the Applicants have found that best results are achieved when the silver used in the plating 20 of the strand is purified to be at least about 98% pure silver, and more preferably at least about 99% pure silver, and most preferably at about 99.99% pure silver.

Purity impacts the efficacy of the device, because the impurities that are contained in less pure silver detract from the antimicrobial properties of the silver. Typically, the impurities that are contained in silver yarn comprise compounds such as lead or cyanide. Lead and cyanide do not allow the neutron with the electrical properties that silver generates, to prevent bacteria from growing. As such, the greater the amount of impurities, the less effective the silver becomes in retarding the growth of microbes. Although it is understood that plated silver monofilament is available from other sources, the present invention is believed to represent the first use of a plated silver nylon mono-filament, wherein the silver is sufficiently pure so as to have significant efficacy when used in connection with a suture product.

Figure 4:
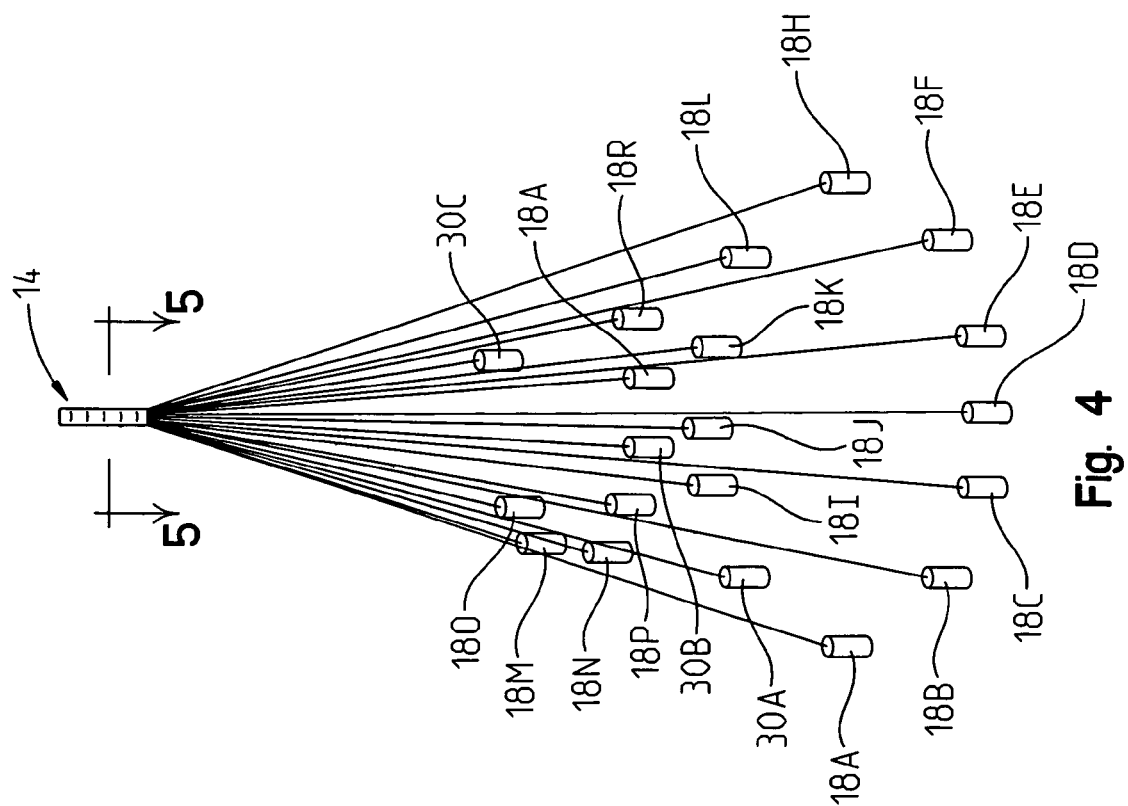
FIG. 4 is a schematic view of a suture forming system, wherein a plurality of spools (a/k/a "cones") that contain representative component threads, along with separation material threads are pulled together to form a cabled suture 14.

FIG. 4 schematically represents the process by which the final cabled suture 14 is produced. In particular, a plurality of strands silver-plated mono-filament 18 are cabled together into the final suture. In addition to the silver-plated monofilament suture 14, a plurality of strands 30*a*-30*c* (here shown as 3) of a separation yarn, such as GRILON® fusible separation yarns, are added into the silver filament cabling.

Separation yarns, such as GRILON® are low melt, multifilaments that, under the influence of heat, such as steam, hot air, or infrared rays, will melt, shrink, and disintegrate into invisible particles. These fusible yarns are available in various melting points, counts and colors. These fusible yarns can be knitted, woven, or stitched. It is then possible to use these yarns precisely and effectively where needed. Typically, GRILON® is used in a fabric, to form an "edge" of the fabric, that resists unraveling. This is not the application to which the GRILON® is used in the present invention. Rather, the GRILON® is used to help prevent the cabled yarn from unraveling.

When one is using very fine monofilament fibers 18 of the type being used with the suture 14 of the present invention, difficulty is encountered when trying to bond the filament threads 18 together into a cabled suture in a manner that makes the cabled suture consistent and resistant to unraveling. Unfortunately, unraveling is a major difficulty that is encountered with cabled sutures.

Through the use of the GRILON® fusible fiber, a permanent bond can be formed between the various monofilaments 18, to thereby help prevent this unraveling. Preferably, the particular GRILON® fusible bonding yarn that is used, is designed to have a melting temperature of approximately 86 degrees F. (30° C.). The 86 degree (30° C.) melting temperature is chosen, so that the GRILON® will melt upon being heated with steam or another heat source in the manufacturing process. Although the Applicant prefers the use of GRILON® brand separation yarn, other separation yarns will likely work.

As best shown in FIG. 4, the GRILON® fibers 30A, 30B, 30C are strategically placed within the realm of silver plated monofilaments that are joined together to form the suture. Through this strategic placement, the separation yarn can bond the various monofilament 18 together in a manner that prevents them from unraveling.

Another section that influences the strategic placement of the separation yarn within the monofilaments is to place the separation yarn filaments within the suture in a manner that it will not coat the silver plating, and thereby prevent the silver on the surface of the monofilaments from killing microbes. As such, one tries to strike a balance in manufacturing a suture, by adding enough separation yarn to bond the suture appropriately, while not adding so much separation yarn that the adhesive within the separation yarn interferes with the ability of the anti-microbial silver to kill microbes. Such interference can occur if the separation yarn material coats the exterior surfaces of the silver-plated monofilaments 18. Preferably, this balance is achieved by causing the GRILON® to be interspersed within the suture 14 cable threads 18, and to not allow the separation yarn to become concentrated at any particular diametric location within the suture.

To manufacture the final suture thread, the suture that includes the silver-plated monofilament along with the yarn separation release filaments, such as the GRILON®, is woven together into a cabled suture 14. The cabled suture 14 is then passed through a heating chamber. Preferably, the heating chamber comprises a Luzy SRL, special heat exchange generator. This generator is discussed in Runkel et al., U.S. Pat. No. 4,641,504, which is incorporated herein by reference.

The heat exchange chamber heats the cabled suture 14 to thereby melt and remove approximately 99% of the separation yarn. Nonetheless, it leaves enough of the separation yarn in the suture to bind the silver plated monofilaments to each other, so that they will not unravel.

Once the suture is finally heated and bonded together, the antimicrobial suture material is sent in a long length roll, to the suture manufacturer. The suture manufacturer cuts the roll of cabled suture "thread" into segments of predetermined sizes to create suture segments of desired lengths. The needle 12 is then added to the cut suture segments. Typically, the finished suture is packed with packaging so that the cabled sutured thread 14 and needle 12 are joined together, and placed in an infection-resistant packet, such as a sterile plastic pouch.

It is believed that the suture 14 so formed will have a look and feel that is generally identical to the current sutures being sold in the market, such as the sutures sold by Johnson & Johnson's ETHICON division. The thread should be strong and pliable.

The suture described above that uses the nylon monofilament that is silver plated is well designed for external sutures. However, modifications may be preferable to employ for sutures that are used internally. For example, rather than using a silver plated nylon monofilament, it may be preferable to use a silver-plated cellulose monofilament, as the cellulose is biodegradable, and thus is more subject to dissolving, thereby obviating the need for removing the sutures from an internal wound.

Additionally, it is believed that a higher concentration of silver should be used on internal threads. Whereas the preferred silver to nylon percentage is somewhere in the 6% to 20% of silver (with 94% to 80% nylon), it may be preferable to use a higher silver concentration, such as a 20%-25% silver (80% to 75% nylon) concentration for internal sutures.

Additionally, it is believed that there will be wide variations in packaging. For example, some packaged sutures may have a suture 14 length of only several centimeters. Other sutures may be extended to be 40 meters long, for tasks that require one very long suture. Examples of various types, sizes and lengths of sutures can be found at a plurality of web sites, such as www.suturedirect.com.

Having described the invention with regard to certain preferred embodiments, it will be appreciated that a wide variety of equivalence and variations can exist that fall within the scope and the spirit of the present invention.

What is claimed:

1. A tissue engageable suture having antimicrobial properties comprising
    a plurality of thread members, the thread members including
    a plurality of structural thread members having a structural portion and an antimicrobial portion, wherein at least a portion of the structural thread members comprise a monofilament core having an exterior surface, and an antimicrobial silver coating applied to the exterior surface to impart antimicrobial properties to the suture,
    a plurality of adhesive thread members comprised of a separation yarn untreated with the antimicrobial silver coating added to the structural thread members in an initial mass,
    wherein the plurality of antimicrobial silver coated structural thread members and the plurality of adhesive thread members are woven together to form a multiple thread-containing cabled suture wherein the adhesive thread members bond the structural thread members within the cabled structure, and wherein the initial mass of separation yarn is reduced by at least about seventy-five percent such that the final mass of the separation yarn remaining in the suture after product completion is less than twenty five percent of the initial mass.

2. The tissue engageable suture of claim 1 wherein the monofilament core comprises a monofilament formed from a material selected from the group consisting of a plastic and a cellulose.

3. The tissue engageable suture of claim 2 wherein the monofilament core has a diameter of between about 2 and 3 decitex.

4. The tissue engageable suture of claim 2 wherein the monofilament core has a diameter of about 2.5 decitex.

5. The tissue engageable suture of claim 1 wherein the silver having antimicrobial properties comprises silver having a purity level of at least about 98% pure silver.

6. The tissue engageable suture of claim 1, wherein the silver comprises silver having a purity level of at least about 99% pure silver.

7. The tissue engageable suture of claim 1 wherein the structural threads comprise, by weight percent between about 75% and 94% structural portion, and between about 6% and 25% silver.

8. The tissue engageable suture of claim 1 wherein the silver comprises by weight percent, between about 6% and 25% of the structural threads.

9. The tissue engageable suture of claim 1 wherein the silver comprises, by weight percent, between about 20% and 25% of the structural thread, and the suture comprises a suture for engaging internal tissue wherein substantially none of the suture resides above a patient's skin.

10. The tissue engageable suture of claim 1 wherein the silver comprises, by weight percent, between about 6% and 20% of the structural thread, and the suture comprises a suture for engaging skin tissue.

11. The tissue engageable suture members of claim 1 wherein the separation yarn members comprise a plurality of separation yarn members interspersed among the structural thread members.

12. The tissue engageable suture members of claim 11 wherein the separation yarn members are made from a material having a melting point of less than about 100° F., such that the application of heat will cause greater than 95% of the mass of the separation yarn material to be removed from the suture.

13. The tissue engageable suture of claim 11 wherein the separation yarn comprises a low melt multi-filament separation yarn having a melting point of less than about 90° F. and being disintegratable under the influence of heat, wherein the application of heat to the suture will cause greater than about 99% of the material of the separation yarn members to be volatilized off the suture.

14. The tissue engageable suture of claim 1 wherein the final mass of the separation yarn remaining in the suture after product completion comprises less than 10 percent of the tissue engageable suture.

15. The tissue engageable suture of claim 1 wherein the final mass of the separation yarn remaining in the suture after product completion comprises less than about 1 percent of the tissue engageable suture.

16. The tissue engageable suture of claim 1 wherein the tissue engageable suture comprises a heat treated cabled suture having at least about 95 percent of its pre-heated weight of separation yarn removed during the heat treating process, such that separation yarn comprises less than about one percent of the post heat treated tissue engageable suture.

17. The tissue engageable suture of claim 16 wherein the silver having antimicrobial properties comprises silver having a purity level of at least about 98% pure silver,
wherein the separation yarn members comprise a plurality of separation yarn members interspersed among the structural thread members, and wherein the separation yarn members are made from a material having a melting point of less than about 100° F., such that the application of heat will cause greater than 75% of the mass of the separation yarn material to be removed from the suture.

18. A tissue engageable suture having antimicrobial properties comprising
a plurality of thread members, the thread members including
a plurality of structural thread members having a structural portion and an antimicrobial portion, wherein at least a portion of the structural thread members comprise a monofilament core having an exterior surface, and an antimicrobial silver coating applied to the exterior surface to impart antimicrobial properties to the suture, wherein the silver applied to the exterior surface has a purity level of at least about 98% pure silver,
a plurality of adhesive thread members comprised of a separation yarn untreated with the antimicrobial silver coating added to the structural thread member in an initial mass,
wherein the plurality of structural thread members and the plurality of adhesive thread members are woven together to form a multiple thread-containing cabled suture wherein the adhesive thread members bond the structural thread members within the cabled structure, and
wherein the initial mass of separation yarn is reduced by at least about seventy-five percent such that the final volume of the separation yarn remaining in the suture after product completion is less than about one percent of the mass of the tissue engageable suture.

* * * * *